(12) United States Patent
Brown

(10) Patent No.: US 10,076,091 B2
(45) Date of Patent: Sep. 18, 2018

(54) POLLEN COMPOSITIONS AND METHODS FOR DISTRIBUTION ON FLOWERING PLANTS

(71) Applicant: POLLEN-TECH LLC, Scottsville, AZ (US)

(72) Inventor: Tom Brown, Mesa, AZ (US)

(73) Assignee: Pollen-Tech LLC, Scottsdale, AZ (US)

(*) Notice: Subject to any disclaimer, the term of this patent is extended or adjusted under 35 U.S.C. 154(b) by 507 days.

(21) Appl. No.: 14/723,733

(22) Filed: May 28, 2015

(65) Prior Publication Data

US 2015/0257345 A1  Sep. 17, 2015

Related U.S. Application Data

(63) Continuation-in-part of application No. PCT/US2013/072500, filed on Nov. 29, 2013.

(60) Provisional application No. 61/883,969, filed on Sep. 27, 2013, provisional application No. 61/730,639, filed on Nov. 28, 2012, provisional application No. 62/003,778, filed on May 28, 2014.

(51) Int. Cl.

| | |
|---|---|
| *A01H 1/02* | (2006.01) |
| *A01N 65/34* | (2009.01) |
| *C12N 5/04* | (2006.01) |
| *A01N 3/00* | (2006.01) |
| *A01N 25/02* | (2006.01) |

(52) U.S. Cl.
CPC ............ *A01H 1/025* (2013.01); *A01N 3/00* (2013.01); *A01N 25/02* (2013.01); *A01N 65/34* (2013.01); *C12N 5/04* (2013.01)

(58) Field of Classification Search
CPC . A01H 1/025; A01H 1/02; A01G 7/00; A01G 1/001; A01G 7/06; A01M 11/00
USPC .......... 47/1.41; 239/142, 303, 304, 310, 311
See application file for complete search history.

(56) References Cited

U.S. PATENT DOCUMENTS

| | | | | |
|---|---|---|---|---|
| 2,548,487 A | * | 4/1951 | Marchant ............... | A01H 1/025 222/174 |
| 2,570,511 A | * | 10/1951 | Blair ...................... | A01H 1/025 102/531 |
| 3,943,660 A | * | 3/1976 | Hosaka .................. | A01H 1/025 222/631 |
| 4,087,937 A | * | 5/1978 | Meader .................. | A01H 1/025 47/1.41 |
| 4,383,389 A | * | 5/1983 | Bezzerides ............ | A01H 1/025 47/1.41 |
| 4,922,651 A | * | 5/1990 | Atkinson ............... | A01G 17/00 47/1.41 |
| 5,689,914 A | * | 11/1997 | Greaves ................. | A01H 1/02 426/419 |
| 6,141,904 A | * | 11/2000 | Greaves ................. | A01H 1/02 47/1.41 |

(Continued)

*Primary Examiner* — Trinh T Nguyen
(74) *Attorney, Agent, or Firm* — Rodney J. Fuller; Booth Udall Fuller, PLC

(57) ABSTRACT

The present invention encompasses a composition comprising a viable pollen suspension in a water miscible carrier. The compositions are especially suitable for mechanical distribution, such as, electrostatic spraying of the viable pollen composition onto a flowering plant to increase pollination. The invention further provides a mechanical system and method for applying droplets containing a viable pollen suspension to flowering plants to increase pollination.

20 Claims, 4 Drawing Sheets

(56) References Cited

U.S. PATENT DOCUMENTS

| | | | |
|---|---|---|---|
| 7,717,353 B2* | 5/2010 | Matulis | A01C 23/008 222/135 |
| 2013/0118066 A1* | 5/2013 | Cope | A01H 1/025 47/1.41 |
| 2013/0118067 A1* | 5/2013 | Cope | A01G 7/00 47/1.41 |
| 2014/0223812 A1* | 8/2014 | Cope | A01H 1/025 47/1.41 |

* cited by examiner

POLLEN COMPOSITIONS AND METHODS FOR DISTRIBUTION ON FLOWERING PLANTS

CROSS-REFERENCE TO RELATED APPLICATIONS

This application is a continuation-in-part of International Application No. PCT/US2013/072500, filed Nov. 29, 2013, which claims the benefit of U.S. Provisional Application No. 61/730,639 filed on Nov. 28, 2012 and U.S. Provisional Application No. 61/883,969 filed on Sep. 27, 2013; and this application also claims the benefit of U.S. Provisional Application No. 62/003,778, filed May 28, 2014, the contents of each of which are hereby incorporated by reference in their entireties for all purposes.

TECHNICAL FIELD

This application relates to the agricultural distribution of pollen compositions on flowering plants to increase pollination of the flowering plants. The present invention specifically relates to the new viable pollen compositions, mechanized distribution systems and methods to enhance and enable mechanical distribution of pollen compositions on flowering plants to reduce risks associated with standard delivery means.

BACKGROUND

Bees pollinate one-third of all the food eaten (1). However, bees are in crisis. They are dying off at record rates from Colony Collapse Disorder (CCD) (2). Millions of dollars of research has gone into this problem of why 30% of the nation's bees are dying off each winter. In the most recent official report, the USDA found no clear cause to the problem, although they listed several factors that may be contributing to the problem (3). These die offs are very sudden as well. Beekeepers can check their hive one day and find their bees healthy, and the next week they find all of them are dead.

This problem could have devastating effects on the nation's food supply. The average die off rate for bees over the past seven years has been approximately 29% (4). This is much higher than 10-15%, which is considered the sustainable loss percentage (5). An insufficient number of bees would result in a loss of crop due to inadequate pollination. Most crops are only partially reliant on bees, and the reduction of colonies will not be catastrophic to the crop but will cause reduction of yield. However, some crops such as almonds are entirely dependent on bee pollination. In fact 60% of the nation's bees are trucked into central California for a short two-week pollination period (6). This means that if there aren't enough bees, almond trees will not be pollinated and almond production will drop. Because of the sudden nature of CCD, some beekeepers found out that their bees had died and they wouldn't be able to keep their bee contracts shortly before the pollination season. This heightens the fears and risks of the almond farmers. Clearly, this is a large problem that could affect the nation's food supply. However, it is bigger than the United States of America. The entire world is struggling with CCD. Therefore, the worldwide crops that rely on insects for pollination are at risk (7).

The problem has compounded as agricultural methods continue to become more densely concentrated. An example of this is the high-density production of almonds in California. Over 90% of all U.S. almond production comes from three counties in California. When it is time to pollinate these crops 60% of all the bees in the U.S. are brought into this one small area of the country. All these bees in one area have lead to problems involving Colony Collapse Disorder. This syndrome occurs when a colony of bees loses over 30% of the bees in a short time. This can come from many sources including transfer of disease and parasites or simple starvation from the lack of plentiful foraging materials. Farmers bring in two or more hives per an acre of almonds to insure complete pollination over the short fertilization season. Almonds are a very early blooming crop and the almonds cover vast areas in an almost monoculture so there is little else for the bees to forage on during this time and can lead to unhealthy conditions and death of bees. There are other substantial risks to the almond growers. These risks include weather, and bee transportation across the country, which involves many logistical risks. Hive disease can mean that even if the bees are transported and the weather cooperates the bees still may not be able to move pollen adequately.

Another economic effect of CCD is that the cost of renting beehives has increased rapidly for many crops such as almonds. Beehive rentals have gone from $100 an acre to the current rate of $350 an acre in just five years (8). This problem has been exacerbated by the fact that due to increased almond demand, the number of almond acres has been increasing thus causing more demand on an increasing limited supply of bees.

Bees have additional risks outside of colony collapse disorder. Even if the bees are at the farm at the appropriate time, there is the risk that the bees will not pollinate the crops during the critical period. Some crops only have a window of two days to pollinate the crops. If the bees do not pollinate the crop during that time due to factors such as disease or poor weather conditions, yield is severely impacted (9). In a good year, the bees may only pollinate up to 10% of the blossoms. Bad weather decreases this significantly. Growers are desperately looking for ways to mitigate these pollination risks.

The bee pollination problem affects an extremely large market. In the US, bee-pollinated crops had a $15 billion value in 2012 (10). The worldwide value of bee-pollinated crops is $217 billion. Almonds, apples, cherries, plums, pears, blueberries, avocados, cantaloupes, cucumber, kiwi, and apricots are a few of the crops that use bees as a pollination method (11). The almond crop is the most affected by the current bee crisis. The almond market is composed of about 6,500 farmers that grow about 810,000 acres of almonds in California (12). The almond industry is also experiencing strong growth with demand growing at 7.3% annually (13). In 2009, the value of the almond harvest was $2.2 billion (14). In 2012, the almond industry's reached $4.1 billion (15). The number of fruit bearing acres increased from 590,000 acres in 2005 to 810,000 acres in 2012 (16).

71% of the almonds grown in California were exported in 2011/2012 (17). 35% of those exports went to Western Europe, 38% to Asia, and 17% to the Middle East (18). China was the largest destination after the United States followed by Spain, India, and Germany (19). Almonds were the most valuable specialty crop exports in the United States and in California the most valuable agricultural export. California grows 80% of the world's almonds.

A need exist for alternative and more reliable means of pollinating almonds and other crops dependent on bees. It is also desirable to find a way to replace or supplement bee pollination to reduce risk and increase profits for the farmers that have relied only on insect pollination in the past.

SUMMARY

The present invention is directed to improved pollen compositions and methods of disbursing viable pollen on a flowering plant. The improved pollen compositions enhance pollen viability duration and/or pollen disbursement via mechanical means, e.g., electrostatic application. The viable pollen compositions preferable include a plurality of viable pollen grains and a combination of at least two water miscible carriers selected from the group consisting of: propylene glycol, glycerol, ethylene glycol, 1,3-butanediol, and 1,4-butanediol and ethyl acetate. In an alternative formulation, the viable pollen compositions includes viable pollen grains and at least one water miscible carrier in an amount of at least 20%, 30%, 40%, 50%, 60%, 70%, 80%, 90%, 95%, or 98% of the pollen composition by weight, wherein the at least one water miscible carrier selected from the group consisting of: propylene glycol, glycerol, ethylene glycol, 1,3-butanediol, and 1,4-butanediol and ethyl acetate, for example, a viable composition comprising at least propylene glycol.

In certain aspects, the composition comprises a plurality of viable pollen grains; and a combination of at least two water miscible carriers selected from the group consisting of: propylene glycol, glycerol, ethylene glycol, 1,3-butanediol, 1,4-butanediol, and ethyl acetate; or at least one water miscible carrier in an amount of at least 40% of the pollen composition by weight, wherein the at least one water miscible carrier is selected from the group consisting of: propylene glycol, glycerol, ethylene glycol, 1,3-butanediol, 1,4-butanediol, and ethyl acetate. In other aspects, the composition comprises a plurality of viable pollen grains; and at least one water miscible carrier selected from the group consisting of: propylene glycol and ethylene glycol.

The at least two water miscible carriers or the at least one water miscible carrier may be any one of propylene glycol and glycerol; glycerol and ethylene glycol; propylene glycol and ethylene glycol; ethyl acetate and glycerol; ethyl acetate and propylene glycol; and ethyl acetate and ethylene glycol.

The composition may further comprise sugars, potassium, calcium, boron, and nitrate ions to promote pollen tube growth. In certain embodiments, the composition further comprises bee attractants. In other embodiments, the composition further comprises antioxidants and/or preservatives.

The present invention is also directed to pollen distribution systems. In certain embodiments, the pollen distribution system comprises: at least a first tank containing a viable pollen composition; a second tank containing an aqueous solution in fluid communication with the first tank; a mixing valve or a mixing tank for mixing the viable pollen composition from the first tank with the aqueous solution from the second tank. The pollen distribution system typically further comprises a spray nozzle in fluid communication with said mixing valve or mixing tank; and optionally, a source of atomizing gas connected to said spray nozzle.

The invention is further directed to methods of disbursing viable pollen on a flowering plant—e.g., almond; cherry; pear; apple; pistachio; plum; peach; apricot, avocado; blueberry; melon; cucumber; cotton; coffee; asparagus; onion; broccoli; alfalfa; soy; celery; tangerine, lemon, strawberry, quince, blackberry, tomatoes, and raspberry. One exemplary method of dispensing viable pollen on a flowering plant comprises the steps of adding an aqueous solution to the viable pollen composition described herein to produce a spray volume; and spraying at least a portion of the spray volume on a flowering plant, thereby dispensing the viable pollen on the flowering plant to pollinate the flowering plant.

Advantageously, in certain embodiments, the viable pollen composition can be dispensed using an electrostatic sprayer. The aqueous solution may be added to the viable pollen composition in an amount of at least 50%, 75%, 85%, 95%, or 97% by weight using a mixing valve or mixing tank prior to spraying on the flowering plant.

In certain embodiments the aqueous solution is added to the viable pollen composition within 5 seconds, 10 seconds, 5 minutes, 15 minutes, 30 minutes, 45 minutes or an hour of spraying the flowing plant with the viable pollen composition.

The invention is also directed to a method of dispensing viable pollen, comprising the steps of: adding a viable pollen composition as described herein to a pollen storage container suitable for connecting to a dispensing device, the viable pollen composition comprising a plurality of viable pollen grains and at least two water miscible carriers selected from the group consisting of: propylene glycol, glycerol, ethylene glycol, 1,3-butanediol, and 1,4-butanediol and ethyl acetate; or at least one water miscible carrier in an amount of at least 20%, 30%, 40%, 50%, or 60% of the viable pollen composition by weight, wherein the at least one water miscible carrier selected from the group consisting of: propylene glycol, glycerol, ethylene glycol, 1,3-butanediol, and 1,4-butanediol and ethyl acetate to create a viable pollen composition; and propelling at least a portion of the viable pollen composition from the pollen storage container using the dispensing device on to a flowering plant to pollinate the flowering plant.

The invention may be used to pollenate any flowering plant including, but not limited to, asterids, rosids, eudicots, and plants from the Rosaceae family.

In certain particular embodiments, the invention provides a method of selecting a liquid medium that easily wets the viable pollen and mixes with it well to form a viable pollen liquid medium. The present invention further provides method of mixing the viable liquid pollen medium with water to form a final composition preferable for method of distribution on flowing plants to increase pollination with our or without the assistance of bee pollination. A preferred group of materials suitable for use herein are primary, secondary and tritiary alcohols as well as ether and ester composition. These may further be defined by the ratio of oxygen to carbon in these compounds. In one embodiment, the preferred mixing materials (e.g., primary, secondary and tertiary alcohols, ethers and esters, have an oxygen:carbon ratio of 1:1 to 1:5, more preferably the mixing materials have a ratio of 1:2 to 1:3 and most preferable the mixing materials have a carbon:oxygen ratio of less than 1:2 for example, 1:1, 1:1.3, 1:1.5, 1:1.8.

To keep pollen alive and viable for extended periods of time the pollen compositions are stored at low temperatures and low humidity levels. In one particular embodiment, the pollen is premixed in a liquid medium, preferably selected from the compounds and compositions taught herein, and then frozen. Storage of pollen in the range of −15 C to −70 C have given excellent long term life results. It however costs more to store large quantities of material at lower temperatures. Thus, in certain embodiments herein, the liquid viable pollen mixture may provide the benefit of allowing freezing at a temperature from 50 C to −70 C, more beneficially from 45 C to −40 C and preferably from 40 C to −15 C; 30 C to −15 C; 20 C to −10 C; 10 C to −5 C. Typically, it is preferred that the pollen is never stored at a temperature above 50 C. The present invention provides several advantages, including allowing the pollen material to be in a frozen state at a higher temperature to reduce the transport costs of refrigeration and to minimize the material being leaked internally into the pollen grain. Solid materials significantly reduce this transport rate.

The transported materials are preferably used in an electrostatic spray operation and thus the material must be transformed into liquid form prior to use while maintaining the pollen viability. A particular method of preparing the viable pollen liquid form includes, first, adding the frozen material directly to water at a preferred liquid temperature, spray temperature, e.g. 10 C, 20 C, 25 C, 30 C. In this embodiment the frozen mixture of pollen dissolves to release the pollen into the spray water. The frozen mixture can be in the form of solid pellets that could be added to a mixing tank or a solid rod could be fed into the mixing tank for example. In the second particular embodiment, the frozen viable pollen mixture is added to a liquid slurry medium at spray temperature and then this two-part slurry is added to a final aqueous liquid phase. Handling issues may be improved when all materials are in a liquid phase as well. The liquid phase can then injected into the spray water a short time before spraying.

DETAILED DESCRIPTION

Figure 1:
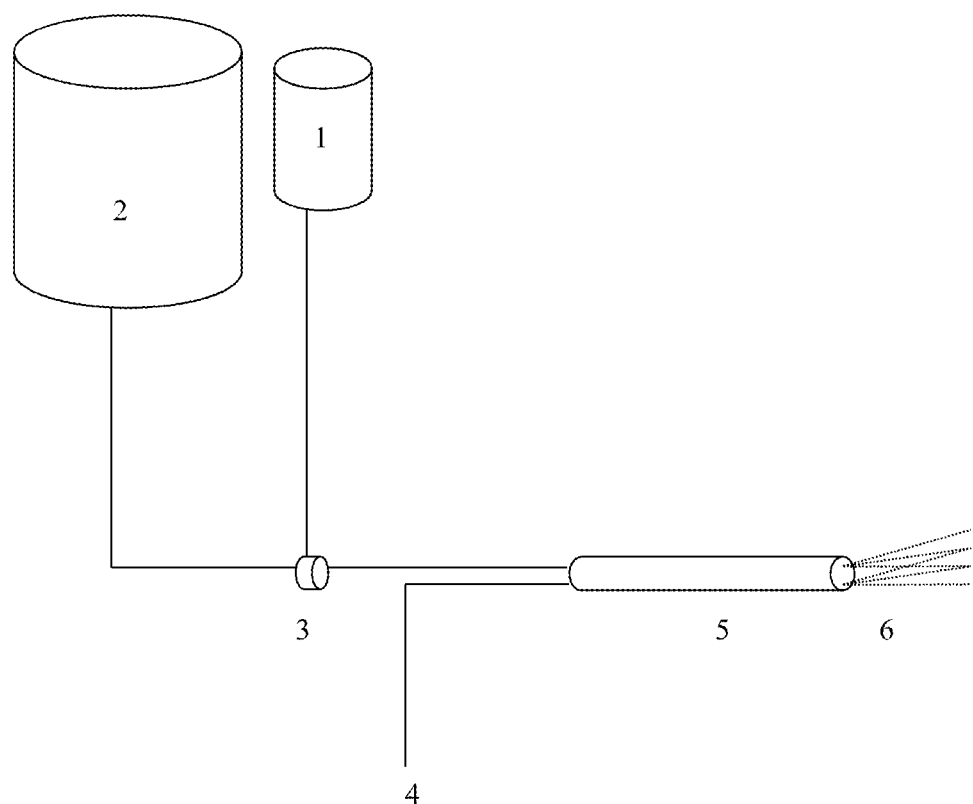
FIG. 1 depicts a system for providing pollen distribution with a first tank (1) containing a pollen suspension, a second tank (2) containing an aqueous solution, and a mixing valve (3) or mixing tank (not shown) joining the two tanks. A spray nozzle (5) is in fluid communication with the mixing valve (3). A source of atomizing gas (4) and the spray (6) leaving the spray nozzle (5) are also shown.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

Viable Pollen Formulations

The present invention provides improved viable pollen compositions that are especially useful for mechanical pollination of flowering plants. The improved pollen compositions are particularly useful with electrostatic application sprayers. An exemplary viable pollen compositions advantageously includes a plurality of viable pollen grains and a combination at least two water miscible carriers selected from the group consisting of: propylene glycol, glycerol, ethylene glycol, 1,3-butanediol, and 1,4-butanediol and ethyl acetate. For example, in certain viable pollen compositions the at least two water miscible carriers is selected from the group consisting of: propylene glycol and glycerol; glycerol and ethylene glycol; propylene glycol and ethylene glycol; ethyl acetate and glycerol; ethyl acetate and propylene glycol; and ethyl acetate and ethylene glycol.

TABLE 1 provides a few preferred formulations for solvent blend based on weight % of each ingredient.

TABLE 1

| Material | Formulation #1 | Formulation #2 | Formulation #3 | Formulation #4 |
|---|---|---|---|---|
| Propylene Glycol | 73% | 41% | | 48% |
| Glycerol | 27% | | 59% | 15% |
| Ethylene Glycol | | 59% | | 32% |
| Ethyl Acetate | | | 41% | 5% |

The propylene glycol, glycerol, ethyl acetate, and/or ethylene glycol in the formulation may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% of the pollen composition by weight. The plurality of pollen grains in the formulation may be about 5%, about 10%, about 15%, about 20%, about 25%, about 30%, about 35%, about 40%, about 45%, or about 50% of the pollen composition by weight.

The plurality of viable pollen grains is generally added to the formulation at between 1% and 40% of the composition by weight, for example, between 5% and 25%, or more specifically, 7.5% and 20%. For instance, in Formulation No. 1, if 5% viable pollen is added to the solvent blend to make the viable pollen composition, there would be 69.5% propylene glycol, 25.65% glycerol and 5% viable pollen based on the weight of the composition.

In certain aspects, the plurality of pollen grains remains viable in the formulation for at least 1 day, at least 2 days, at least 3 days, at least 4 days, at least 5 days, at least 6 days, or at least 7 days.

In some embodiments, the composition of the present invention comprises a viable pollen suspension that contains at least 1,000,000 pollen grains, 50,000,000 pollen grains, at least 80,000,000 pollen grains, at least 100,000,000 pollen grains, at least 150,000,000 pollen grains, at least 200,000,000 pollen grains, at least 2,500,000,000 pollen grains, at least 5,000,000,000 pollen grains, at least 7,500,000,000 pollen grains, at least 10,000,000,000 pollen grains, or at least 15,000,000,000 pollen grains per liter. When an aqueous solution is added to the viable pollen composition in preparation for distribution on a flowing plant, the amount of pollen per liters diluted according to the amount of aqueous solution added. For example, at least 45, 50, or 100 million pollen grains per liter after mixing with the aqueous solution.

In alternative formulations, the viable pollen compositions include viable pollen grains and at least one water miscible carrier in an amount of at least 20%, 30%, 40%, 50%, 60%, 70%, 75%, or 80% of the pollen composition by weight, wherein the at least one water miscible carrier selected from the group consisting of: propylene glycol, glycerol, ethylene glycol, 1,3-butanediol, and 1,4-butanediol and ethyl acetate, for example, a viable composition comprising propylene glycol in an amount that is at least 35% of the composition by weight.

The viable pollen composition typically comprises less than 10% water by weight of the composition, e.g., less than 5%, 3%, 1%, or 0.5%, before preparation for distribution and use for pollination of flowing plants. An aqueous solution is typically added to the viable pollen composition within 5 seconds, 10 seconds, 5 minutes, 30 minutes, 45 minutes, or an hour of preparation and the mechanical distribution of the viable pollen on the flowing plant. The amount of aqueous solution (e.g., water) added to the viable pollen composition in preparation for distribution is generally in amount between, 99.9% and 60%; more specifically more than 75%, 80%, 90%, 95%, or 99%.

The plurality of viable pollen grains is preferably from an eudicot, e.g., an asterid or rosid. Specific examples of pollen grain suitable for use in the compositions include: almond; cherry; pear; apple; pistachio; plum; peach; apricot, avocado; blueberry; melon; cucumber; cotton; coffee; asparagus; onion; broccoli; alfalfa; soy; celery; tangerine, lemon, strawberry, quince, blackberry, and raspberry pollen.

Advantageously the viable pollen composition has a density suitable for a type of pollen added. For example, for almond the pollen composition is prepared so that it has a density of between 1.00 g/cc and 1.20, more specifically between 1.03 g/cc and 1.12 g/cc, more preferably between 1.05 g/cc and 1.10 g/cc, for example, about 1.08 g/cc.

Additional ingredients and additives can be advantageously added to the composition of the present invention may further contain sugars, potassium, calcium, boron, and nitrates. These additives may promote pollen tube growth after pollen distribution on flowering plants. Bee attractants may also be included. Known bee attractants include pheromones and essential plant oils. A "pheromone" is a natural or synthetic chemical substance that triggers a response in members of a species. One example of a pheromone that can be used in the present invention is the Nasonov (alternatively, Nasanov) pheromone, which is released by worker bees to orient returning forager bees back to the colony. Nasonov includes nerol, (E,E)-farnesol, geraniol, nerolic acid, citral and geranic acid. Ingrid H. Williams, et al., The Nasonov pheromone of the honeybee (hymenoptera, apidae). Part II. Bioassay of the components using foragers. *Journal of Chemical Ecology,* 7(2):225-237, March 1981. Bees use Nasonov to find the entrance to their colony or hive, and they release it on flowers so other bees know which flowers have nectar. Synthetic versions of Nasonov may contain any one of the chemical compounds present in natural Nasonov or any combination of these chemical compounds. For example, one synthetic version of Nasonov pheromone consists of citral and geraniol in a 2:1 ratio.

Essential oils producing fragrances found in highly scented flowers, for example, may also be used in the composition of the present invention. Chemoreceptors in their antennae cause bees to seek out these fragrances. One essential oil that may be used is essential oil of anise. Honeybees can identify the fragrance from a few drops of essential oil of anise from a considerable distance.

In some embodiments, the composition of the present invention contains dehydrated or partially dehydrated viable pollen.

Under ordinary conditions of storage and use, the composition of the present invention may contain a preservative to prevent the growth of microorganisms. The preventions of the action of microorganisms can be brought about by various antibacterial and antifungal agents, for example, parabens, chlorobutanol, sorbic acid, and the like. Antioxidants may also be added to the pollen suspension to preserve the pollen from oxidative damage during storage. Suitable antioxidants include, for example, ascorbic acid, tocopherol, sulfites, metabisulfites such as potassium metabisulfite, butylhydroxytoluene, and butylhydroxyanisole.

Methods of Viable Pollen Distribution and Pollination by Mechanical Means

The invention also provides methods of dispensing viable pollen on a flowering plant. The disclosed electrostatic pollination application process may be used on any bee-pollinated plant.

In one embodiment, the method comprises adding an aqueous solution to the viable pollen composition of the invention to produce a spray volume; and spraying at least a portion of the spray volume on a flowering plant, thereby dispensing the viable pollen on the flowering plant to pollinate the flowering plant. The aqueous solution is generally added to the viable pollen composition in an amount of at least 50% (e.g., at least 65%, 75%, 85%, 95%, 98%, 99%, 99.5% by weight) using a mixing valve and/or a mixing tank prior to disperse on the flowering plant at least a portion of the spray volume on a flowering plant. In certain embodiments an electrostatic sprayer is used to spray at least a portion of the spray volume on a flowering plant. The aqueous solution is added to the viable pollen composition within 5 seconds, 10 seconds, 5 minutes, 10 minutes, 30 minutes, 45 minutes or an hour of spraying the flowing plant with the viable pollen composition. A mixing tank can be used to mix the water and viable pollen composition prior to distribution. The length of time that the pollen is in the aqueous mixture affects viability of the pollen.

In another embodiment, the method of dispensing viable pollen comprises the steps of adding a viable pollen composition to a pollen storage container suitable for connecting to a dispensing device, the viable pollen composition comprising a plurality of viable pollen grains and a combination of at least two water miscible carriers selected from the group consisting of: propylene glycol, glycerol, ethylene glycol, 1,3-butanediol, and 1,4-butanediol and ethyl acetate; or at least one water miscible carrier in an amount of at least 20%, 30%, 40%, 50%, or 60% of the viable pollen composition by weight, wherein the at least one water miscible carrier selected from the group consisting of: propylene glycol, glycerol, ethylene glycol, 1,3-butanediol, and 1,4-butanediol and ethyl acetate to create a viable pollen composition; followed by the step of propelling at least a portion of the viable pollen composition from the pollen storage container using the dispensing device on to a flowering plant to pollinate the flowering plant.

In a preferred embodiment, the invention further comprises mixing the viable pollen composition with an aqueous solution from a second container using a mixing valve and/or a mixing tank prior to propelling at least a portion of the viable pollen composition on the flowering plant. As in some of the other embodiments, the aqueous solution is mixed with the viable pollen composition within 5 seconds, 10 seconds, 5 minutes, 15 minutes, 30 minutes, 45 minutes or an hour of dispersing the viable pollen aqueous mixture on a flowing plant.

In one preferred embodiment, the viable pollen mixture is mechanically dispersed using an electrostatic sprayer. The dispensing nozzle preferably used in mechanical distribution of the viable pollen mixture forms viable pollen droplets upon spraying or propelling the viable pollen composition onto the flowering plant. The ratio of the viable pollen droplet volume compared to the volume of the viable pollen grain is less than 1.5:1, less than 2.0:1, less than 2.5:1, less than 3.0:1, less than 3.5:1, less than 4.0:1, less than 4.5:1, less than 5.5:1, less than 6.0:1, less than 6.5:1, less than 7.0:1, less than 7.5:1, less than 8.0:1, less than 8.5:1, less than 9.0:1, less than 9.5:1, or less than 10.0:1. In one example, the ratio of the viable pollen droplet volume compared to the volume of the viable pollen grain is less than 3.0:1.

The methods of the invention may further comprise adding a bee attractant to the pollen suspension and an electrostatic sprayer is used to spray at least a portion of the spray volume on a flowering plant.

In some embodiments, the droplets containing the pollen suspension are applied to a group of flowering plants within 1 day, 2 days, 3 days, 4 days, 5 days, 6 days, or 1 week to allow for uniform maturing of the flowering plants. The applying the droplets containing the pollen suspension may occur after induction of the flowering plants to produce flowers.

The method of the present invention may further comprise adding a bee attractant to the pollen suspension. The resulting droplets may then be applied to flowering plants and bees allowed to contact the flowering plants to increase the efficiency of pollination. Small water droplets containing sugars and/or pollen can be extremely stimulating to bee activity. Spraying with this mixture when flowers are mature may lead to increased pollination through increased bee activity.

In yet other embodiments, the droplets containing the pollen suspension are applied in the absence of bees to increase homogeneity in resulting fruits and/or seeds. Often the random pollination by natural vectors such as bees is undesirable because it can lead to mixed genetic products. By using netting or other bee exclusion devices including distance and by pollinating with a spray it is possible to more carefully control the pollen fertilization product.

The methods of the invention generally are directed to dispensing viable pollen on a flowering plant that is a eudicot, for example, an asterid or rosid and more specifically a plant from the Rosaceae family. Non-limiting examples of flowering plants suitable for use with the methods described herein include: almond; cherry; pear; apple; pistachio; plum; peach; apricot, avocado; blueberry; melon; cucumber; cotton; coffee; asparagus; onion; broccoli; alfalfa; soy; celery; tangerine, lemon, strawberry, quince, blackberry, and raspberry pollen.

The plurality of viable pollen grains in the viable pollen composition is chosen based on what flowering plant the viable pollen mixture will be dispensed on. For example, when the plurality of viable pollen grains in the viable pollen mixture are almond or cherry, the viable pollen mixture will be dispersed on an almond or cherry plant respectively.

One non-limiting specific example of the disbursement amounts of the viable pollen composition on the flowering plant in grams per acre is shown below in Table 2—disbursement preferable occurs soon after mixing with water to preserve viability.

TABLE 2

| Ingredient | Grams/acre | % of solution |
| --- | --- | --- |
| Water | 15,220 | 97.5% |
| Water miscible carrier | 350 | 2.2% |
| Pollen | 50 | 0.3% |

Systems for Providing Pollen Distribution

In some embodiments, the invention is a system for providing pollen distribution comprising: a first tank (1) containing a pollen suspension in a water miscible carrier; a second tank (2) containing an aqueous solution in fluid communication with said first tank; a mixing valve (3) or a mixing tank (not shown) joining the pollen suspension from said first tank and the aqueous solution from said second tank; a spray nozzle (5) in fluid communication with said mixing valve; and optionally, a source of atomizing gas (4) connected to said spray nozzle.

In the embodiment shown in FIG. 1 there are two tanks: one holding the pollen suspension (1) and one holding the aqueous born materials (2). The carrier for the pollen suspension has the desirable properties of being water miscible and not harmful to the pollen suspended. The aqueous tank holds the water for the spray volume. Either tank may also contain nutrients and growth factors for pollen tube growth. These nutrients include: sugars, potassium, calcium, boron, and nitrate ions and other desirable materials. The outlets from the aqueous and non-aqueous tanks combine at a mixing valve (3) or a mixing tank (not shown). The two components mix here and then move to the spray nozzle (5). An additional input to the nozzle can be a source of atomized gas such as compressed air (4). In certain embodiments that comprise a mixing tank, the mixing tank is used to allow the aqueous solution to be mixed with the viable pollen composition for at least 5 seconds, 5 minutes, 15 minutes, 30 minutes, 45 minutes or 55 minutes. A mixing value (3) can be used in conjunction with a mixing tank for delay in of disbursement of the viable pollen mixture to provide certain benefits of bringing the viable pollen in contact with water for a short time, without compromising the viability of the pollen.

Figure 2:
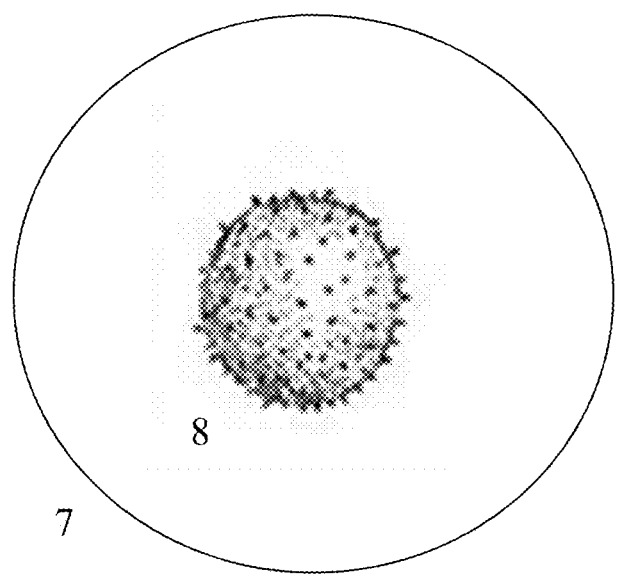
FIG. 2 depicts a pollen grain (8) inside a droplet (7) after leaving the spray nozzle. The drop may be electrostatically charged as a result of ionization or induction produced at the spray nozzle.

Two dominant methods of producing very small spray droplets are by having a high liquid pressure drop through the nozzle or by using a high velocity air stream going through the nozzle and removing liquid from an orifice. The fine spray leaving the nozzle can be charged by ions created in the nozzle by a potential difference induction or corona discharge. In one embodiment, the droplets are as small as practical while still holding the pollen. The droplet weight to charge density is a ratio that may impact how quickly the droplet will attach to the plant being pollinated. In some embodiments, the diameter of the droplet to the diameter of the pollen grain is about 1.5:1, about 2.0:1, about 2.5:1, about 3.0:1, about 3.5:1, about 4.0:1, about 4.5:1, or about 5.0:1. FIG. 2 shows a droplet (7) and a pollen grain (8) at the preferred ratio are such that the droplet is small as possible and still able to transmit the pollen grain. One example, is about 3.0:1 for the diameter of the droplet to the diameter of the pollen grain. In other embodiments, the volume of the droplet to the volume of the pollen grain is about 1.5:1, about 2.0:1, about 2.5:1, about 3.0:1, about 3.5:1, about 4.0:1, about 4.5:1, about 5.5:1, about 6.0:1, about 6.5:1, about 7.0:1, about 7.5:1, about 8.0:1, about 8.5:1, about 9.0:1, about 9.5:1, or about 10.0:1.

In some aspects of the invention, the spray nozzle is a single-fluid nozzle. Single-fluid or hydraulic spray nozzles utilize the kinetic energy of the liquid to break it up into droplets. As the fluid pressure increases in a single-fluid nozzle, the flow through the nozzle increases, and the drop size decreases. Many configurations of single fluid nozzles may be used with the invention.

In one embodiment, the single-fluid nozzle is a plain orifice nozzle. The pressure drop applied may be high (e.g., at least about 25 bar) so that the material is finely atomized. In other embodiments, the single-fluid nozzle is a shaped orifice nozzle. The shaped orifice may use a hemispherical shaped inlet and a "V" notched outlet to cause the flow to spread out on the axis of the V notch. The single-fluid nozzle may also be a surface impingement nozzle, which causes a stream of liquid to impinge on a surface resulting in a sheet of liquid that breaks up into drops. In certain embodiments, the impingement surface may be formed in a spiral to yield a spiral shaped sheet approximating a full cone spray pattern or a hollow-cone spray pattern. The spiral design generally may produce a smaller drop size than the pressure swirl type nozzle design, for a given pressure and flow rate. This design is clog resistant due to the large free passage.

In yet other embodiments, the single-fluid nozzle may be a pressure-swirl spray nozzle. The stationary core of a pressure-swirl spray nozzle induces a rotary fluid motion, which causes the swirling of the fluid in the swirl chamber. A film is discharged from the perimeter of the outlet orifice producing a characteristic hollow cone spray pattern. Air or other surrounding gas is drawn inside the swirl chamber to form an air core within the swirling liquid. Many configurations of fluid inlets may be used to produce this hollow cone pattern. In another embodiment, the single-fluid nozzle may be a spill-return pressure-swirl single-fluid nozzle. This nozzle is one variety of pressure swirl nozzle that includes a controlled return of fluid from the swirl chamber to the feed system that allows the nozzle pressure drop to remain high while allowing a wide range of operating rates.

In one embodiment, the single-fluid nozzle is a solid cone single-fluid nozzle. In this nozzle, the swirling liquid motion is induced with a vane structure, but the discharge flow fills the entire outlet orifice. For the same capacity and pressure drop, a full cone nozzle will produce a larger drop size than a hollow cone nozzle.

In another embodiment, the spray nozzle may be a two-fluid nozzle. Two-fluid nozzles atomize a liquid by causing the interaction of an atomizing gas with the liquid. Compressed air is most often used as the atomizing gas, but sometimes steam or other gases are used. The many varied designs of two-fluid nozzles can be grouped into internal mix or external mix depending on the mixing point of the gas and liquid streams relative to the nozzle face.

In some embodiments, the invention includes a two-fluid nozzle that is an internal mix two-fluid nozzle where fluids make contact inside the nozzle. Shearing between high velocity gas and low velocity liquid may disintegrate the liquid stream into droplets, producing a high velocity spray. The internal mix nozzle may use less atomizing gas than an external mix atomizer and is better suited to higher viscosity streams.

In other embodiments, the invention includes a two-fluid nozzle that is an external-mix two-fluid nozzle. With external mix nozzles the fluids make contact outside the nozzle. External-mix two-fluid nozzles may require more atomizing air and a higher atomizing air pressure drop because the mixing and atomization of liquid takes place outside the nozzle.

In certain embodiments of the invention, the spray nozzle is a compound nozzle. A compound nozzle is a type of nozzle in which several individual single-fluid nozzles or two-fluid nozzles are incorporated into one nozzle body. Compound nozzles allow for design control of drop size and spray coverage angle.

In some embodiments of the invention, the spray nozzle may produce electrostatic charging of fluid as the fluid leaves the spray nozzle. The viable pollen compositions described herein are well suited for use in an electrostatic sprayer. An electric potential difference may be created in the nozzle resulting in a corona discharge and ionization of the spray and droplets leaving the nozzle. Electrostatic charging of sprays is very useful for high transfer efficiency. The charging is typically at high voltage (e.g., 1.5 KV to about 20 kV to about 40 kV) but low current.

In other embodiments, the invention may include a spray nozzle with rotary atomizers. Rotary atomizers use a high speed rotating disk, cup or wheel to discharge liquid at high speed to the perimeter, forming a hollow cone spray. The rotational speed controls the drop size. The invention may also include a spray nozzle with ultrasonic atomizers, which utilize high frequency (e.g., about 20 kHz to about 50 kHz) vibration to produce narrow drop-size distribution and low velocity spray from a liquid. The vibration of a piezoelectric crystal causes capillary waves on the nozzle surface liquid film.

In certain embodiments, a mixing paddle is used in the system to ensure the pollen grains remain suspended in the slurry. The mixing paddle along with the similar densities between water miscible carriers and the pollen grains prevent the pollen grains from settling out of the slurry mixture or rising to the top of the mixture.

In one embodiment, the slurry is mixed with the water in the system before being sprayed and is applied to the plants within a matter of seconds after mixing with water. For example, there may be a delay of about 5 seconds, about 10 seconds, about 20 seconds, about 30 seconds, about 40 seconds, about 50 seconds, or about 60 seconds between the time the slurry is mixed with water and the time that it is applied to plants.

The contents of all references, patents, and published patent applications cited throughout this application, as well as the Figures, are incorporated herein by reference in their entirety for all purposes.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1

Field Trial with Mechanical Pollination of Almond Trees

Materials and Methods

Figure 3:
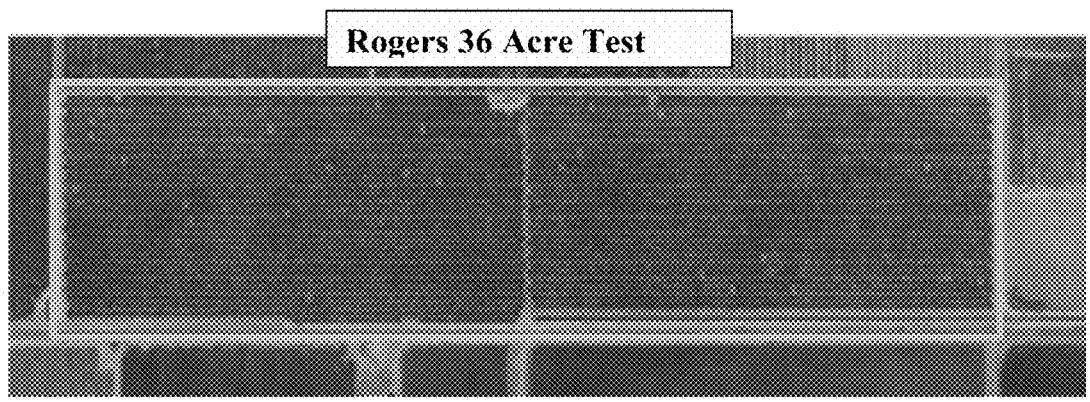
FIG. 3 depicts the thirty-six acre test plot of almond trees near Madera, Calif. where trees were treated with 10 grams of pollen per acre or 40 grams of pollen per acre and the resulting almond yields were measured and compared to untreated controls.

The test was conducted on almonds *Prunus dulcis* that are pollinated with the honeybees, *Apis mellifera*, at 1.75 hives per acre and nine frames of bees per hive. The pollen used in the experiment was N+.Pe.PD pollen obtained from Firman Pollen, e.g., Neplus Ultra (50% match Nonpareil, 50% match Monterey); Peerless (100% match Nonpareil, 50% match Monterey); Padre (100% match Nonpareil, 50% match Monterey). The sprayer used to distribute the pollen was provided by Electrostatic Spray Systems (ESS). Rows used in the experiment were 2376 feet long and had 140 trees spaced 17 feet apart down the row. Rows were 22 feet apart and one row was 1.200 acres. Rows 2-27 were used in the test (see FIG. 3). Rows 1, 28, 29, 30 were excluded for being partial rows and on the perimeter. The field consists of Non-Pareil almond variety on the even rows and Monterey variety planted on the odd rows. On the Monterey rows every 10th tree was replaced with the Carmel variety of almonds. The field was located near Madera, Calif.

Pollen was mixed into a slurry mixture made from a base slurry mixture comprising 100% glycerol, with future slurry mixtures to be tested later comprising 23% w/w glycerol and 77% w/w propylene glycol. The final slurry mixture contained between about 10% w/w and 25% w/w pollen grains diluted in the base slurry. The slurry mixture was pumped into a water stream that goes to spray nozzles where the liquid is electrostatically charged. The amount of water added to the slurry was based on the tractor speed. In the experimental design, tractor speed was really a pseudonym variable for amount of water added. The objective was to minimize water added during spray and to measure to see the effect. For example, a tractor travelling half the speed with same pollen delivery would require twice the volume of water added.

Air pressurized by a turbo charger blew the electrostatically charged liquid out of the nozzle and to the trees. The pollen was attracted electrostatically to the tree branches and especially to the stigma of the flower where pollination was completed. The water spray had an additive to decrease osmotic pressure on the pollen. Sucrose was added at a 10% level to the water to decrease the osmotic pressure. The water spray rate was about 9 gallons per acre.

Figure 4:
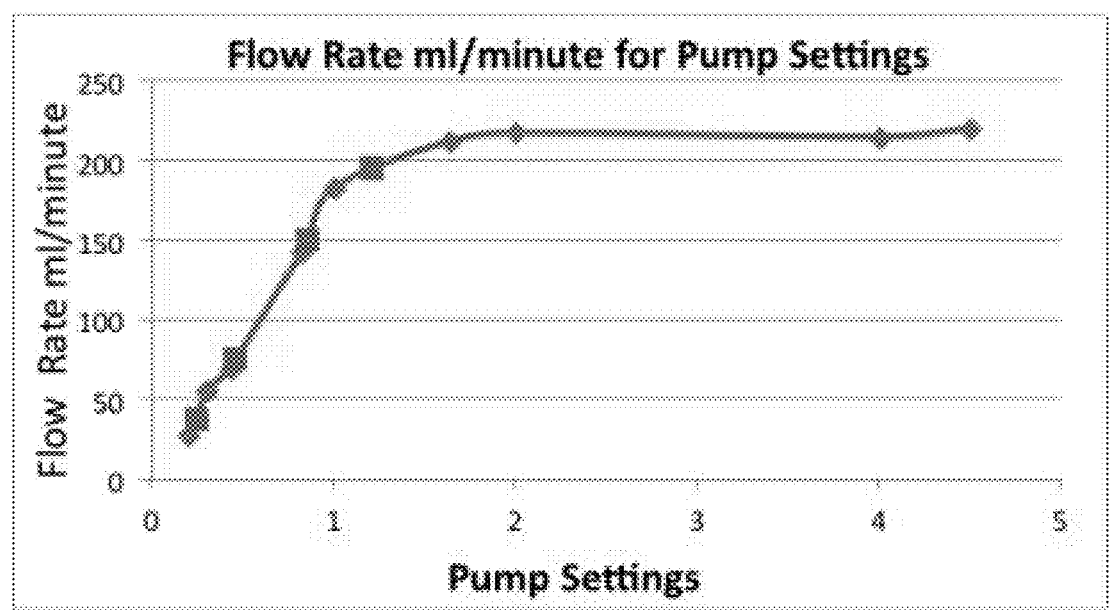
FIG. 4 depicts the flow rate (mL/min) at the various pump settings for application of the pollen in the slurry mixture during the field trials in the almond grove near Madera, Calif.

The pump had an adjustable piston stroke so that the amount of pollen slurry delivered to the water stream going to the nozzles could be controlled. Due to the high viscosity of the fluid, the maximum flow rate was at less than a setting of 2.0 with 10.0 being the highest setting. The flow rate achieved by the various pump settings is shown in FIG. 4. The relatively low flow rate required a reduction in the tractor speed during the test.

The tractor pulling the spray equipment traveled at 4.3 miles per hour for all conditions except where the pollen was delivered at 20 g per pass. This was the highest delivery rate for the pollen and the tractor had to go down a gear to travel at 2.8 mph to maintain the necessary power take-off (PTO) shaft speed for the correct air pressure. The pollen slurry was pumped at the required speed to give the desired delivery of pollen per acre.

At harvest the experiment was adjusted due two issues. A balance couldn't be obtained to measure each row weight as originally had been planned. This limitation caused weights to be determined as a whole experimental block and didn't allow us to measure the row-to-row variability within a block. Secondly there was a miscommunication between the experimenter and the farmers so that several rows of Non-Pareil were harvested and mixed in a way that reduced the reliability of the 40 g/acre sections of the Non-Pareil experiment. Some of these results were added back in on a best estimation basis.

The experiment was set up as a $2^2$ full factorial design with a control. There were three replicates for each of the four conditions. The control was limited to one row each of the Monterey and Non-Pareil. After eliminating the outside rows we divided the remaining rows for treatment as shown in TABLE 3. Pollination spray dates were on three consecutive days (for the three spays).

TABLE 3

|  | 10 g/acre | 40 g/acre |
|---|---|---|
| Monterey |  |  |
| 2 sprays | Rows 17, 19, 21 (Group III) | Rows 23, 25, 27 (Group IV) |
| 3 sprays | Rows 9, 11, 13 (Group II) | Rows 3, 5, 7 (Group I) |

TABLE 3-continued

|  | 10 g/acre | 40 g/acre |
|---|---|---|
| Non-Pareil |  |  |
| 2 sprays | Rows 16, 18, 20 (Group III) | Rows 22, 24, 26 (Group IV) |
| 3 sprays | Rows 8, 10, 12 (Group II) | Rows 2, 4, 6 (Group I) |
| Control | Monterey | Non-Pareil |
|  | Row 15 | Row 14 |

Results

The almond yields from trees sprayed with 10 grams of pollen per acre and those sprayed with 40 grams per acre are compared to untreated controls in TABLE 4. An increase in yield was observed in trees sprayed with pollen, and this effect was more pronounced at the higher rate of application of 40 grams of pollen per acre. There was also a trend in the date indicating that fewer spraying applications seemed to more effectively enhance yield.

TABLE 4

|  | 10 g/acre | 40 g/acre |
|---|---|---|
| Monterey |  |  |
| 2 sprays | 39160 lbs/3.6 acres | 42960 lbs/3.6 acres |
| 3 sprays | 39000 lbs/3.6 acres | 42043 lbs/3.6 acres |
| Non-Pareil |  |  |
| 2 sprays | 42590 lbs/3.6 acres | 45182 lbs/3.6 acres |
| 3 sprays | 43640 lbs/3.6 acres | 44553 lbs/3.6 acres |
| Control | Monterey | Non-Pareil |
|  | 40320 lbs/3.6 acres | 44925 lbs/3.6 acres |

TABLES 5 and 6 indicate the differences in yield between almond trees treated with 10 grams of pollen per acre and those treated with 40 grams of pollen per acre and those treated with two sprays versus those treated with three sprays, respectively.

TABLE 5

|  | 10 g/acre | 40 g/acre | Difference between 10 g and 40 g per acre |
|---|---|---|---|
| Monterey |  |  |  |
| 2 sprays | −2.88% | +6.55% | 9.43% |
| 3 sprays | −3.27% | +4.27% | 7.54% |
| Average | −3.08% | +5.41% | 8.5% |
| Non-Pareil |  |  |  |
| 2 sprays | −5.2% | +0.6%* | 5.8% |
| 3 sprays | −2.9% | −0.8%* | 2.10% |
| Average | −4.0% | −0.1% | 3.90% |
| Overall Average | −3.5% | +2.6% | 6.1% |

*These data points are less reliable.

TABLE 6

|  | 2 sprays | 3 sprays | Difference between 2 sprays and 3 sprays |
|---|---|---|---|
| Monterey |  |  |  |
| 10 g/Acre | −2.88% | −3.27% | 0.39% |
| 40 g/Acre | +6.55% | +4.27% | 2.28% |
| Average |  |  | 1.34% |
| Non-Pareil |  |  |  |
| 10 g/Acre | −5.2% | −2.9% | −2.30% |
| 40 g/Acre | +0.6%* | −0.8%* | 1.40% |
| Average |  |  | −0.45% |
| Overall Average |  |  | +0.44% |

*These data points are less reliable

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. United States Department of Agriculture: Agriculture Research Service. Honey Bees and Colony Collapse Disorder. Retrieved Sep. 25, 2013, from http://www.ars.usda.gov/News/docs.htm?docid=15572
2. National Bee Health Stakeholder Conference Steering Committee, Report on the Nation Conference on Honey Bee Health, 2012
3. United States Department of Agriculture: Agriculture Research Service. Honey Bees and Colony Collapse Disorder. Retrieved Sep. 25, 2013, from http://www.ars.usda.gov/News/docs.htm?docid=15572
4. National Bee Health Stakeholder Conference Steering Committee, Report on the Nation Conference on Honey Bee Health, 2012
5. National Bee Health Stakeholder Conference Steering Committee, Report on the Nation Conference on Honey Bee Health, 2012
6. United States Department of Agriculture: Agriculture Research Service. Honey Bees and Colony Collapse Disorder. Retrieved Sep. 25, 2013, from http://www.ars.usda.gov/News/docs.htm?docid=15572
7. Helmholtz Association of German Research Centres (2008, Sep. 15). Economic Value Of Insect Pollination Worldwide Estimated At U.S. $217 Billion. *ScienceDaily*. Retrieved Sep. 25, 2013, from http://www.sciencedaily.com/releases/2008/09/080915122725.htm
8. Sumner, Daniel A and Hayley Boriss. Bee-conomics and the Leap in Pollination Fees. Retrieved Sep. 25, 2013, from http://aic.ucdavis.edu/research/bee-conomics-1.pdf; Woodbridge, Terry. Almond Pollination 2013: Update on almond pollination prices. Dec. 22, 2012. Retrived Sep. 25, 2013, from http://woodbridgebee.com/media/2012_press/Almond_Pollination_2013_Update_on_almond_pollination_prices.html
9. Law, S. E. (2001). Agricultural electrostatic spray application: a review of significant research and development during the 20th century. Journal of Electrostatics, 51, 25-42,
10. United States Department of Agriculture: Agriculture Research Service. Honey Bees and Colony Collapse Disorder. Retrieved Sep. 25, 2013, from http://www.ars.usda.gov/News/docs.htm?docid=15572
11. Moisset, Beatriz and Stephen Buchmann. Bee Basics: An Introduction to Our Native Bees. A USDA Forest Service and Pollinator Partnership Publication. Retrived Sep. 25, 2013, from http://www.fs.usda.gov/Internet/FSE_DOCUMENTS/stelprdb5306468.pdf
12. Almond Conference, Economics of Almond Production, 2012, Slide 4
13. Almond Conference, Economics of Almond Production, 2012, Slide 15
14. United States Department of Agriculture National Agriculture Statistics Services, 2013 Almond Forecast, 2013
15. United States Department of Agriculture National Agriculture Statistics Services, 2013 Almond Forecast, 2013
16. United States Department of Agriculture National Agriculture Statistics Services, 2013 Almond Forecast, 2013
17. Almond Board of California, 2012 Almond Almanac, 2012, pg 9-15
18. Almond Board of California, 2012 Almond Almanac, 2012, pg 9-15
19. Almond Board of California, 2012 Almond Almanac, 2012, pg 9-15

What is claimed is:

1. A system for providing pollen distribution comprising:
a first tank containing a pollen suspension in a water miscible carrier;
a second tank containing an aqueous solution in fluid communication with said first tank;
a mixing valve, a mixing tank, or both, joining the pollen suspension from said first tank and the aqueous solution from said second tank to form a viable pollen composition;
a spray nozzle in fluid communication with said mixing valve;
a source of atomizing gas connected to said spray nozzle; and
at least one mixing blade, agitator, or both, associated with the first tank, the mixing tank or both, and wherein the viable pollen suspension comprises a plurality of onion, cotton, almond or cherry viable pollen grains and one or more sugars, and potassium, calcium, boron, and nitrate ions.

2. The system of claim 1, wherein the viable pollen composition comprises propylene glycol and less than 10% water by weight and more than 30% ethylene glycol or propylene glycol by weight.

3. A system for providing pollen distribution comprising:
a first tank containing a pollen suspension in a water miscible carrier;

a second tank containing an aqueous solution in fluid communication with said first tank;

a mixing valve, a mixing tank, or both, joining the pollen suspension from said first tank and the aqueous solution from said second tank to form a viable pollen composition; and a spray nozzle in fluid communication with said mixing valve, wherein the water miscible carrier includes a combination of at least two water miscible carriers selected from the group consisting of: propylene glycol, glycerol, ethylene glycol, 1,3-butanediol, 1,4-butanediol, and ethyl acetate; or at least one water miscible carrier selected from the group consisting of: propylene glycol and ethylene glycol; or at least one water miscible carrier in an amount of at least 40% of the viable pollen composition by weight, wherein the at least one water miscible carrier is selected from the group consisting of: propylene glycol, glycerol, ethylene glycol, 1,3-butanediol, 1,4-butanediol, and ethyl acetate.

4. The system of claim 3, wherein the viable pollen composition comprises at least 50% ethylene glycol or propylene glycol by weight.

5. The system of claim 1, wherein the pollen suspension in a water miscible carrier comprises:

a plurality of viable pollen grains; and an organic water miscible carrier in an amount of at least 10% of the pollen composition by weight; or a combination of at least two water miscible carriers selected from the group consisting of: propylene glycol, glycerol, ethylene glycol, 1,3-butanediol, 1,4-butanediol, and ethyl acetate; or at least one water miscible carrier selected from the group consisting of: propylene glycol and ethylene glycol; or at least one water miscible carrier in an amount of at least 40% of the pollen composition by weight, wherein the at least one water miscible carrier is selected from the group consisting of: propylene glycol, glycerol, ethylene glycol, 1,3-butanediol, 1,4-butanediol, and ethyl acetate.

6. The system of claim 5, wherein the viable pollen composition comprises propylene glycol.

7. The system of claim 5, wherein the viable pollen composition comprises less than 10% water by weight and more than 30% ethylene glycol or propylene glycol by weight.

8. The system of claim 7, wherein the viable pollen composition comprises at least 50% ethylene glycol or propylene glycol by weight.

9. The system of claim 8, wherein the plurality of viable pollen grains are onion, cotton, almond or cherry pollen, the viable pollen composition further comprises one or more sugars, and potassium, calcium, boron, and nitrate ions.

10. The system of claim 9, further comprising calcium ions; and bee attractants selected from the group consisting of: pheromones, essential plant oils, and combinations thereof; and at least $2.5 \times 10^9$ pollen grains per liter.

11. The system of claim 5, wherein the plurality of viable pollen grains is between about 5% and about 25% of the composition by weight.

12. The system of claim 5, wherein the at least two water miscible carriers or the at least one water miscible carrier is selected from the group consisting of: propylene glycol and glycerol; glycerol and ethylene glycol; propylene glycol and ethylene glycol; ethyl acetate and glycerol; ethyl acetate and propylene glycol; and ethyl acetate and ethylene glycol.

13. The system of claim 12, wherein propylene glycol, glycerol, ethyl acetate, and/or ethylene glycol is at least 40% of the pollen composition by weight.

14. The system of claim 13, wherein the viable pollen composition has a density of between 1.03 g/cc and 1.12 g/cc; propylene glycol, glycerol, ethyl acetate, and/or ethylene glycol is at least 50% of the viable pollen composition by weight; and the plurality of viable pollen grains are almond or cherry.

15. The system of claim 3, wherein the pollen suspension in a water miscible carrier comprises:

a plurality of viable pollen grains; and an organic water miscible carrier in an amount of at least 10% of the pollen composition by weight; or a combination of at least two water miscible carriers selected from the group consisting of: propylene glycol, glycerol, ethylene glycol, 1,3-butanediol, 1,4-butanediol, and ethyl acetate; or at least one water miscible carrier selected from the group consisting of: propylene glycol and ethylene glycol; or at least one water miscible carrier in an amount of at least 40% of the pollen composition by weight, wherein the at least one water miscible carrier is selected from the group consisting of: propylene glycol, glycerol, ethylene glycol, 1,3-butanediol, 1,4-butanediol, and ethyl acetate.

16. The system of claim 15, wherein the viable pollen composition comprises propylene glycol.

17. The system of claim 15, wherein the viable pollen composition comprises less than 10% water by weight and more than 30% ethylene glycol or propylene glycol by weight.

18. The system of claim 17, wherein the viable pollen composition comprises at least 50% ethylene glycol or propylene glycol by weight.

19. The system of claim 18, wherein the plurality of viable pollen grains are onion, cotton, almond or cherry pollen, the viable pollen composition further comprises one or more sugars, and potassium, calcium, boron, and nitrate ions.

20. The system of claim 8, further comprising calcium ions; and bee attractants selected from the group consisting of: pheromones, essential plant oils, and combinations thereof; and at least $2.5 \times 10^9$ pollen grains per liter.

* * * * *